United States Patent
Kim et al.

(10) Patent No.: US 10,883,128 B2
(45) Date of Patent: Jan. 5, 2021

(54) METHOD OF PRODUCING GENTIOBIOSE OR GLUCOSE FROM β-GLUCAN USING β-1,6-ENDOGLUCANASE

(71) Applicant: Korea University Research and Business Foundation, Seoul (KR)

(72) Inventors: Kyoung Heon Kim, Seoul (KR); Damao Wang, Seoul (KR); Do Hyoung Kim, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/315,039

(22) PCT Filed: Jun. 30, 2017

(86) PCT No.: PCT/KR2017/006950
§ 371 (c)(1),
(2) Date: Jan. 3, 2019

(87) PCT Pub. No.: WO2018/008900
PCT Pub. Date: Jan. 11, 2018

(65) Prior Publication Data
US 2019/0309334 A1    Oct. 10, 2019

(30) Foreign Application Priority Data
Jul. 7, 2016   (KR) .................. 10-2016-0085868

(51) Int. Cl.
| | | |
|---|---|---|
| *C12P 19/02* | (2006.01) | |
| *C12N 9/24* | (2006.01) | |
| *C12N 15/52* | (2006.01) | |
| *C12P 19/14* | (2006.01) | |
| *C12P 19/12* | (2006.01) | |
| *C07H 3/02* | (2006.01) | |

(52) U.S. Cl.
CPC ............... *C12P 19/02* (2013.01); *C07H 3/02* (2013.01); *C12N 9/24* (2013.01); *C12N 15/52* (2013.01); *C12P 19/12* (2013.01); *C12P 19/14* (2013.01); *C12Y 302/01006* (2013.01)

(58) Field of Classification Search
None
See application file for complete search history.

(56) References Cited

U.S. PATENT DOCUMENTS 6,022,723 A    2/2000   Kofod et al.

OTHER PUBLICATIONS

Accession Q21GC8. Apr. 18, 2006 (Year: 2006).*
Ko et al. Bioprocess Biosyst Eng. Apr. 2016;39(4):677-84. Epub Jan. 25, 2016 (Year: 2016).*
Hong Wu et al., "Purification and Characterization of β-1,6-Glucanase of Streptomyces rochei Application in the Study of Yeast Cell Wall Proteins", Bioscience, Biotechnology, and Biochemistry, Jul. 15, 2002, pp. 2515-2519, vol. 66, No. 11.
NCBI, putative retaining b-glycosidase [Saccharophagus degradans 2-40], GenBank: Accesion, ABD82251.1, Feb. 10, 2014, 2 pages.
Machiko Takahashi et al., "Biochemical characterization of Magnaporthe oryzae β-glucosidases for efficient β-glucan hydrolysis", Applied Microbiology Biotechnology, May 29, 2011, pp. 1073-1082, vol. 91.
Damao Wang et al., "A Novel Glycoside Hydrolase Family 5 β-1,3-1,6-Endoglucanase from Saccharophagus degradans 2-40$^T$ and Its Transglycosylase Activity", Applied and Environmental Microbiology, Jul. 2016, pp. 4340-4349, vol. 82, No. 14.
International Search Report for PCT/KR2017/006950 dated Oct. 31, 2017 [PCT/ISA/210].

* cited by examiner

*Primary Examiner* — Christian L Fronda
(74) *Attorney, Agent, or Firm* — Sughrue Mion, PLLC

(57) ABSTRACT

The present invention relates to a novel β-1,6-endoglucanase producing gentiobiose or glucose from β-glucan, and more specifically, the present invention provides an effect of producing gentiobiose or glucose at high yield through β-1,6-endoglucanase showing β-1,6-endoglucanase activity on β-glucan.

4 Claims, 6 Drawing Sheets

Specification includes a Sequence Listing.

SEQUENCE LISTING

<160> NUMBER OF SEQ ID NOS: 4

<210> SEQ ID NO 1
<211> LENGTH: 481
<212> TYPE: PRT
<213> ORGANISM: Saccharophagus degradans 2-40T

<400> SEQUENCE: 1

Met Thr Leu Leu Lys Asn Ile Asn Lys Gln Arg Leu Ala Arg Lys Val
1               5                   10                  15

Lys Leu Val Cys Ser Ala Ile Ser Leu Val Val Met Gly Phe Ser Cys
            20                  25                  30

Ala Ala Ser Ala Asn Gln Tyr Trp Leu Thr Ser Gly Asp Leu Ser Ala
        35                  40                  45

Ala Phe Glu Glu Gln Gly Glu Lys Tyr Ala Val Ala Pro Ser Pro Glu
    50                  55                  60

Met Pro Leu Ile Thr Ile Asp Lys Ser Gln Ala Phe Gln Thr Met Glu
65                  70                  75                  80

Gly Phe Gly Tyr Thr Leu Asn Gly Gly Ser Ala Thr His Leu Ala Asn
                85                  90                  95

```
Met Ser Asp Ala Ala Arg Ala Arg Leu Leu Gln Glu Ile Phe Gly Gln
            100                 105                 110

Ser Asp Gly Ala Asn Thr Asn Lys Pro Ser Ile Gly Val Ser Tyr Leu
        115                 120                 125

Arg Leu Ser Leu Gly Ala Ser Asp Leu Asp Pro Ala Pro Phe Ser Tyr
    130                 135                 140

Asn Asp Leu Pro Pro Gly Glu Val Asp Leu Lys Leu Glu Lys Phe Thr
145                 150                 155                 160

Ile Ala Gln Asp Glu Lys Thr Leu Ile Pro Ile Leu Lys Gln Ile Leu
                165                 170                 175

Ala Ile Asn Pro Asn Ile Thr Phe Met Ala Ser Pro Trp Ser Pro Pro
            180                 185                 190

Val Trp Met Lys Thr Asn Gly Ser Thr Ile Gly Gly Glu Leu Asn Pro
        195                 200                 205

Glu Tyr Tyr Ser Val Tyr Ala Gln Tyr Phe Val Lys Tyr Val Gln Ala
    210                 215                 220

Met Ala Glu His Gly Ile Asn Ile Asp Ala Ile Thr Ile Gln Asn Glu
225                 230                 235                 240

Pro Met His Pro Gly Asn Asn Pro Ser Leu Leu Met His Ala Lys Asp
                245                 250                 255

Gln Ala Asp Phe Ile Ala Asn His Leu Gly Pro Ala Phe Lys Gln Ala
            260                 265                 270

Glu Leu Lys Thr Lys Ile Ile Val Trp Asp His Asn Ala Asp Lys Pro
        275                 280                 285

Glu Tyr Pro Ile Glu Val Leu Asn His Pro Val Ala Asn Gln Tyr Ile
    290                 295                 300

His Gly Ser Ala Phe His Leu Tyr Gly Gly Asp Val Asn Ala Ile Ser
305                 310                 315                 320

Gln Val His Asn Ala His Pro Asp Lys His Leu Tyr Phe Thr Glu Gln
                325                 330                 335

Trp Val Gly Ala Asn Ser Asn Phe Trp Gly Asp Val Ala Trp His Val
            340                 345                 350

Glu Asn Leu Ile Val Gly Ala Thr Arg Asn Trp Cys Lys Thr Val Leu
        355                 360                 365

Glu Trp Asn Leu Ala Ala Asp Ser Asn Leu Gln Pro His Thr Leu Gly
    370                 375                 380

Gly Cys Asp Ala Cys Leu Gly Ala Leu Thr Ile Asp Gly Asp Asn Val
385                 390                 395                 400

Lys Arg Asn Ala Ala Tyr Tyr Ile Ile Ala His Ala Ala Lys His Val
                405                 410                 415

Pro Pro Gly Ser Val Arg Ile His Ser His Arg Val Ala Gly Leu Pro
            420                 425                 430

Asn Val Ala Phe Leu Thr Pro Gln Lys Lys Val Val Val Val Val Leu
        435                 440                 445

Asn Asn Thr Thr Gln Leu Gln Ser Phe Thr Leu Val His Asp Arg Gln
    450                 455                 460

Lys Phe Ala Tyr Ser Met Pro Ala Gln Ser Val Val Thr Leu Val Ile
465                 470                 475                 480

Asp

<210> SEQ ID NO 2
<211> LENGTH: 1446
<212> TYPE: DNA
<213> ORGANISM: Saccharophagus degradans 2-40T
```

<400> SEQUENCE: 2

```
atgacgttac taaaaaatat aaataagcaa cgcctagcac gtaaagttaa actcgtctgt      60
agcgcgataa gcctagtggt tatggggttc agctgtgccg cgtcagccaa tcaatactgg     120
ttaaccagcg gtgatctaag tgcggcgttc gaagagcagg gcgaaaagta cgcggtagct     180
cccagccccg aaatgcccct tattaccata gataaaagcc aagcatttca aaccatggaa     240
ggctttggct ataccttaa tggcggcagt gcaactcacc tagccaatat gagtgacgca      300
gctagagcgc ggctattaca agaaatattt ggtcaaagtg atggtgcgaa tactaataag     360
cccagtattg gcgtgtctta tttgcgttta agcctaggcg catcagattt agaccccgcc     420
ccgtttagct acaacgattt gccgcctggc gaagtggatt taaagctaga aaaatttact     480
atcgcccaag atgaaaaaac tcttatcccc atacttaagc aaatattagc tattaaccca     540
aatattacat ttatggctag cccttggtct ccgcctgtat ggatgaaaac aaacggctct     600
accattggtg gtgagctaaa cccagaatac tacagcgtat atgcacaata ttttgttaaa     660
tatgttcaag caatggctga gcacggcata aacatagatg ccattactat tcaaaatgaa     720
cctatgcacc cgggtaataa cccaagcttg ctcatgcatg caaagatca agccgacttt      780
attgctaatc acttaggccc cgcgtttaag caggcagagc taaaaacaaa aatcattgtg     840
tgggatcaca acgcagacaa acccgaatac cccatagagg tactgaatca ccccgttgcc     900
aatcaatata ttcacggctc ggcattccat ttatatggcg gcgatgtaaa tgccataagc     960
caagtgcaca atgctcaccc agataagcac ttatattta ctgagcagtg ggtaggcgca     1020
aattccaact tttggggcga tgtagcttgg catgtagaaa atttaattgt tggggcaacc    1080
cgcaattggt gcaaaacggt attggagtgg aatttagccg cagacagtaa cttacagcct    1140
cacactcttg gtggatgcga cgcctgctta ggcgcgctaa ctattgatgg cgataacgtg    1200
aagcgcaatg ccgcgtatta cattattgcc cacgcagcta acatgtacc gccaggctcg     1260
gtgcgtatcc attcgcaccg tgtggcgggt ttacctaatg ttgctttct tacgccgcag     1320
aaaaaggttg ttgtagtagt gcttaataat actactcaat tacagtcatt tacattggtg    1380
cacgaccgtc aaaagtttgc ctattccatg cccgcacaga gcgttgtaac gctagttata    1440
gattaa                                                              1446
```

<210> SEQ ID NO 3
<211> LENGTH: 57
<212> TYPE: DNA
<213> ORGANISM: Artificial Sequence
<220> FEATURE:
<223> OTHER INFORMATION: Forward prime

<400> SEQUENCE: 3

```
gcgggatccc accaccaca ccaccaccaa tactggttaa ccagcggtga tctaagt          57
```

<210> SEQ ID NO 4
<211> LENGTH: 57
<212> TYPE: DNA
<213> ORGANISM: Artificial Sequence
<220> FEATURE:
<223> OTHER INFORMATION: Reverse primer

<400> SEQUENCE: 4

```
gcgctcgagg tggtggtggt ggtggtgatc tataactagc gttacaacgc tctgtgc          57
```

METHOD OF PRODUCING GENTIOBIOSE OR GLUCOSE FROM β-GLUCAN USING β-1,6-ENDOGLUCANASE

CROSS REFERENCE TO RELATED APPLICATIONS

This application is a National Stage of International Application No. PCT/KR2017/006950 filed Jun. 30, 2017, claiming priority based on Korean Patent Application No. 10-2016-0085868 filed Jul. 7, 2016.

BACKGROUND

1. Field of the Invention

The present invention relates to a novel β-1,6-endoglucanase producing gentiobiose or glucose from β-glucan.

2. Discussion of Related Art

β-glucan has long been widely used for applications such as antioxidant effects, anticancer functionality, skin protecting agents, and the like.

β-glucans are divided into β-1,3-glucan, β-1,4-glucan, and β-1,6-glucan according to the type of linkages constituting the polymer, and β-1,6-glucan is known to exist in nature in a small amount as compared to other β-1,3- or β-1,4-linkages. Pustulan derived from *Lasallia pustulata* is a well-known representative example of β-1,6-glucan, and laminarin is also well known as β-1,3-1,6-glucan constituting brown algae.

β-1,6-glucanases are known to randomly cleave β-1,6-glycosidic linkages of β-glucan, and according to Carbohydrate Active enZYmes database (CAZy; http://www.cazy.org/), β-1,6-glucanases are known to belong to the glycoside hydrolase (GH) families 5 and 30. β-1,6-glucanases derived from fungi have been reported mainly as β-1,6-glucanase, and there has been no report of bacterial β-1,6-glucanases to date.

SUMMARY OF THE INVENTION

An object of the present invention is to provide a use of a novel β-1,6-endoglucanase capable of producing gentiobiose or glucose from β-glucan.

To achieve the above-described objective, the present invention provides a composition for producing gentiobiose or glucose, including a β-1,6-endoglucanase including amino acid sequences set forth in SEQ ID NO: 1, wherein the β-1,6-endoglucanase uses, as a substrate, one or more selected from the group consisting of laminarin and pustulan.

The present invention also provides a method of producing gentiobiose or glucose, including reacting a β-1,6-endoglucanase including amino acid sequences set forth in SEQ ID NO:1 with, as a substrate, one or more selected from the group consisting of laminarin and pustulan.

The present invention provides a β-1,6-endoglucanase exhibiting β-1,6-endoglucanase activity with respect to β-glucan.

The β-1,6-endoglucanase can use laminarin or pustulan as a substrate, thus providing an effect of producing gentiobiose or glucose with a high yield.

DETAILED DESCRIPTION OF EXEMPLARY EMBODIMENTS

Figure 1:
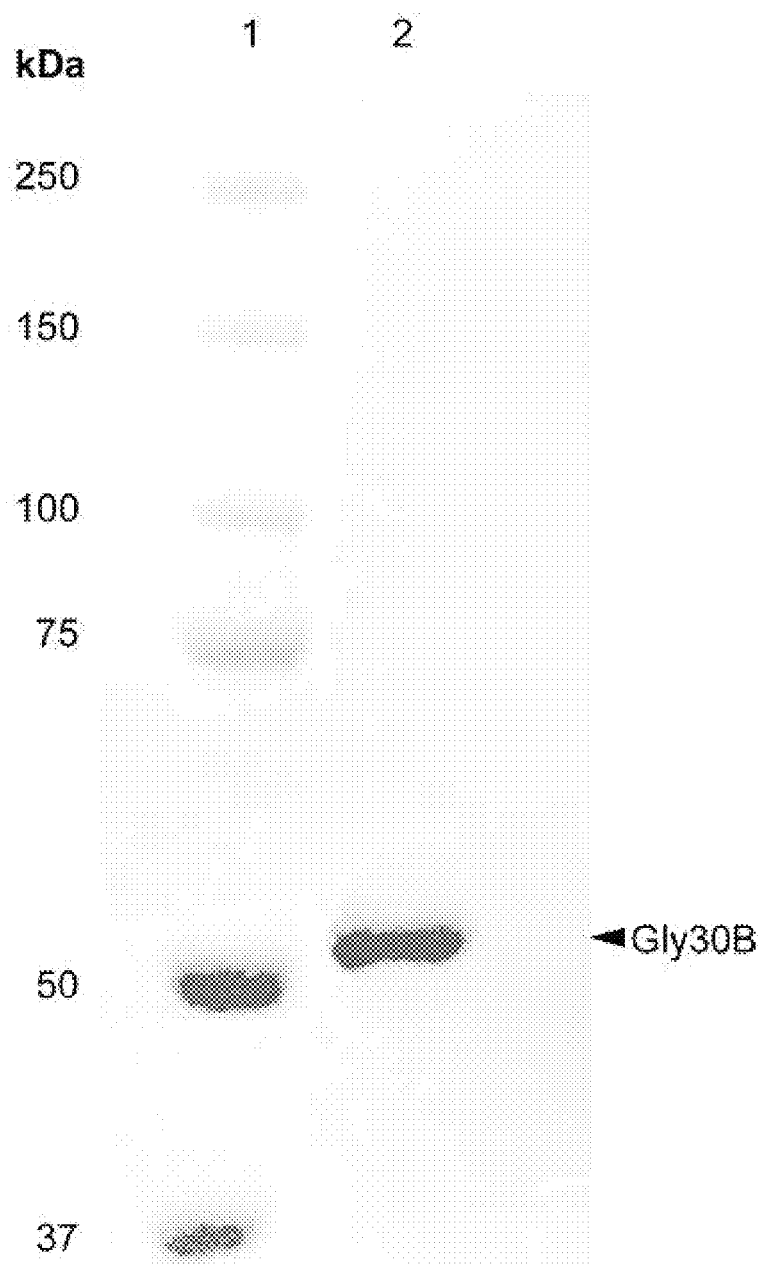
FIG. 1 is a gel electrophoretic photograph of confirming the expression of the β-1,6-endoglucanase of the present invention.

The inventors of the present invention confirmed the β-glucan degrading activity of the Gly30B protein belonging to the GH30 family, which is assumed to have β-glycosidase activity. As a result, the Gly30B protein used, as a substrate, laminarin which is a polysaccharide composed of a β-1,3-linked glucose main chain and β-1,6-linked glucose branches to cleave the β-1,6-glycosidic linkages of laminarin, thereby producing gentiobiose or glucose, and cleaved the β-1,6-glycosidic linkages of pustulan which is a polysaccharide composed of β-1,6-linked glucose, thereby producing gentiobiose or glucose.

Therefore, the present invention provides a composition for producing gentiobiose or glucose, which includes a β-1,6-endoglucanase having amino acid sequences set forth in SEQ ID NO: 1, wherein the β-1,6-endoglucanase uses, as a substrate, one or more selected from the group consisting of laminarin and pustulan.

The present invention also provides a method of gentiobiose or glucose, including reacting a β-1,6-endoglucanase having amino acid sequences set forth in SEQ ID NO: 1 with one or more substrates selected from the group consisting of laminarin and pustulan.

The β-1,6-endoglucanase exhibits β-1,6-endoglucanase activity with respect to β-glucan.

The β-1,6-endoglucanase maintains thermal stability at a temperature ranging from about 20° C. to about 45° C., and exhibits an optimum degrading activity with respect to laminarin or pustulan. More particularly, the β-1,6-endoglucanase may exhibit an optimum activity at a temperature of about 20° C. to about 40° C.

In addition, the optimum pH of the β-1,6-endoglucanase in a buffer may vary depending on the type of the buffer, and may range from about 4 to about 10, more particularly about 6 to about 8, and most particularly about 7.

The β-1,6-endoglucanase may use laminarin, pustulan, or the like as a substrate.

A reaction product of the enzyme may be gentiobiose or glucose with a degree of polymerization of 2.

The β-1,6-endoglucanase may be derived from *Saccharophagus degradans* 2-40$^T$, but the present invention is not particularly limited thereto.

In addition, the β-1,6-endoglucanase may be transcribed and translated through a coding gene, which is a DNA fragment associated with the production of a polypeptide including regions upstream and downstream of a coding region of the enzyme and an intervening sequence between individual coding fragments. For example, the β-1,6-endoglucanase may be transcribed and translated from sequences set forth in SEQ ID NO: 2, but the present invention is not particularly limited thereto. In addition, mutant proteins differing from the aforementioned enzyme by one or more substitutions, deletions, translocations, additions, and the like and having the oligosaccharide or glucose hydrolytic activity are also encompassed within the scope of the enzyme of the present invention, and they preferably have an amino acid sequence with at least 80% homology, at least 85% homology, at least 90% homology, at least 93% homology, at least 94% homology, at least 95% homology, at least 96% homology, at least 97% homology, at least 98% homology, and at least 99% homology, to the amino acid sequences set forth in SEQ ID NO: 1.

The β-1,6-endoglucanase may be separated from a supernatant of the *Saccharophagus degradans* 2-40$^T$ culture broth and purified, or may be produced and separated from strains other than *Saccharophagus degradans* 2-40$^T$ using a genetic recombination technique or produced and separated by an artificial chemical synthesis method.

When the recombination technique is used, typical factors used to facilitate expression of recombinant proteins, e.g., antibiotic-resistant genes, and reporter proteins or peptides that may be used for affinity column chromatography, may be used, and such a technique falls within the scope of the present invention that may be easily carried out by one of ordinary skill in the art to which the present invention pertains. For example, the β-1,6-endoglucanase may be obtained from host cells transfected into a recombinant vector including a nucleic acid encoding the β-1,6-endoglucanase, i.e., base sequences set forth in SEQ ID NO: 2, or a cultured product thereof. *E. coli* may be used as the host cells, but the present invention is not limited thereto.

The reaction of the β-1,6-endoglucanase with the substrate may be performed at a temperature ranging from 20° C. to 45° C. and a pH of 5 to 10 for 5 minutes to 1 day. More particularly, when laminarin or pustulan is used as the substrate, the reaction may be performed at a temperature ranging from 30° C. to 40° C. and a pH of 6 to 8 for 5 minutes to 5 hours.

A degradation product of the enzyme may be sequentially subjected to silica gel chromatography, which is adsorption chromatography, and Biogel P2 chromatography, which is gel permeation chromatography, thereby isolating and purifying an oligosaccharide or glucose with a high purity of about 95%.

The terms "protein" and "polypeptide" as used herein are used interchangeably.

In the present invention, a polypeptide having a sequence identity of certain percentage (e.g., 80%, 85%, 90%, 95%, or 99%) with respect to another sequence means that, when the two sequences are aligned with respect to each other and compared, the two sequences have identity in amino acid resides by the mentioned percentage. The alignment and percentage homology or identity may be determined using any proper software program known in the art, for example, one described in [CURRENT PROTOCOLS IN MOLECULAR BIOLOGY (F. M. Ausubel et al., (eds) 1987 Supplement 30 section 7.7.18)]. Preferable programs include GCG Pileup programs, FASTA (Pearson et al., 1988 *Proc. Natl Acad. Sci USA* 85:2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25:3389-3402). Another preferable alignment program is ALIGN Plus (Scientific and Educational Software, PA), which preferably uses basic parameters. Still another suitable sequence software program is the TFASTA Data Searching Program available for Sequence Software Package Version 6.0 (Genetics Computer Group, University of Wisconsin, Madison, Wis.).

In the present invention, the term "recombination" used in connection with cells, nucleic acids, proteins, or vectors means that the cells, nucleic acids, proteins, or vectors are modified by introduction of heterogeneous nucleic acids or proteins, or alteration of innate nucleic acids or proteins, or that the cells are derived from such modified cells. That is, the recombinant cells, for example, express genes which would not be found in cells in their original (non-recombinant) forms, or express the original genes which wound be expressed abnormally or would not have been expressed at all.

In the present specification, the term "nucleic acid" encompasses all kinds of single- or double-stranded DNAs, RNAs, and chemical variants thereof. The terms "nucleic acid" and "polynucleotide" may be used interchangeably herein. Since genetic codes are degenerated, one or more codons may be used to encode a certain amino acid, and the present invention encompasses polynucleotides encoding certain amino acid sequences.

The term "introduction" used to describe insertion of a nucleic acid sequence into cells refers to "transfection," "transformation," or "transduction," and encompasses reference to integration of a nucleic acid sequence into eukaryotic or prokaryotic cells. In this case, the nucleic acid sequence is integrated into the genome (for example, a chromosome, a plasmid, a chromatophore, or mitochondrial DNA) of cells, and it is converted into an autonomous replicon or expressed temporally.

EXAMPLES

Hereinafter, the present invention will be described in further detail with reference to the following examples. However, these examples are not intended to limit the scope of the present invention.

<Example 1> Obtainment of Gly30b Gene Via Cloning

A putative β-1,6-endoglucanase (Sde_2994), which was derived from *Saccharophagus degradans* 2-40$^T$ (ATCC 43961), was cloned into *Escherichia coli* DH5α. A more specific description is as follows.

*Saccharophagus degradans* 2-40$^T$ (ATCC 43961) was cultured in a minimum medium containing 23 g/L of an instant seawater salt, 50 mM Tris-HCl, 2 g/L of glucose, 2 g/L of a yeast extract, and 0.5 g/L of ammonium chloride at 30° C. for 12 hours.

The genomic DNA of *Saccharophagus degradans* 2-40$^T$ (ATCC 43961) was obtained using a commercially available DNA isolation kit (Qiagen, Valencia, Calif., USA).

The target gene gly30b (GenBank ID ABD82251.1) was amplified using Solg 2×Taq PCR smart mix 2 (SolGent, Daejeon, Korea). The used primers are as follows:

```
Forward primer:
                                     (SEQ ID NO: 3)
5'-GCGGGATCCCACCACCACCACCACCACCAATACTGGTTAACCAGCGG
TGATCTAAGT-3';
and
```

-continued

Reverse primer:
(SEQ ID NO: 4)
5'-GCGCTCGAGGTGGTGGTGGTGGTGATCTATAACTAGCGTTACAACGCTCTGTGC-3'.

These primers have restriction enzyme sites BamHI and XhoI at the 5' terminal. In addition, to increase the affinity of a HisTrap column, the base sequence of a gene encoding histidine was added.

The PCR product and the vector pET28a were double-digested with BamHI and XhoI, and the final DNA fragment was ligated. The plasmid carrying Gly30b was transformed into *Escherichia coli* DH5a.

<Example 2> Overexpression and Purification of Gly30B Protein

To overexpress the gene obtained according to Example 1, the gene was transformed into *Escherichia coli* BL21(DE3), which is a host for protein expression.

The cells were incubated at 37° C. until absorbance at 600 nm reached 0.6, using Luria-Bertani (LB) broth (BD, Sparks, Md., USA) supplemented with 50 mg/L of kanamycin. Protein expression was induced using 0.1 mM IPTG and the induction temperature was set at 16° C. to express the recombinant protein in a water-soluble form.

To isolate the expressed Gly30B protein, the cells were disrupted by ultra-sonication and centrifuged, and then the supernatant was purified using a HisTrap column (GE Healthcare, Piscataway, USA). The purified protein was concentrated with an Amicon Ultra Centrifugal filter (millipore, Billerica, Mass., USA). The molecular weight of the expressed Gly30B protein was measured as being approximately 52 kDa by SDS-PAGE (see FIG. 1). The concentration of the protein was measured using a bicinchoninic acid (BCA) protein assay kit (Pierce, Rockford, Ill., USA).

<Example 3> Verification of Substrate Specificity and Cationic Effect of Gly30B Protein To confirm the enzymatic activity of the Gly30B protein, 1.89 nM of the Gly30B protein was allowed to react in 100 µl of 20 mM Tris-HCl (pH 6.0) containing a substrate such as pustulan, laminarin (Wako, Osaka, Japan), or the like at 2% at 40° C. for 30 minutes. In addition, to confirm the substrate specificity of the Gly30B protein, 10.5 µM of the Gly30B protein was allowed to react in 100 µl of 20 mM Tris-HCl (pH 6.0) containing various glucans such as pustulan, laminarin, curdlan (Wako, Osaka, Japan), carboxymethyl cellulose (Sigma-Aldrich, St Louis, Mo., USA), xylan (Sigma-Aldrich, St Louis, Mo., USA), and the like at 40° C. for 30 minutes. The produced reducing sugars were measured using a DNS method.

As shown in Table 1 below, the Gly30B protein showed the highest activity with respect to pustulan, and when laminarin was used as the substrate, it exhibited a relative activity of about 22%, as compared to when pustulan alone was used as the substrate. The Gly30B protein was confirmed not to hydrolyze curdlan, and this confirms that the Gly30B enzyme selectively cleaved β-1,6-glucan linkages. In addition, the Gly30B protein was found not to react with β-1,4-glycosidic bonds such as in Avicel, CM-cellulose, and xylan.

As a result of examining cationic effects of the Gly30B protein, it was confirmed that the reactivity of the Gly30B protein was inhibited by cations such as $Ni^{2+}$, $Cu^{2+}$, $Fe^{2+}$, and $Mg^{2+}$, and among these, inhibited most by $Cu^{2+}$ (see Table 2).

TABLE 1

Substrate Specificity of Gly30B Protein

| Substrate | Type of glucosidic bond in the main chain | Monosaccharides | Relative enzymatic activity (%) |
|---|---|---|---|
| Pustulan | β-1,6 | Glucose | 100 |
| Laminarin | β-1,3: β-1,6 | Glucose | 22.37 |
| Curdlan | β-1,3 | Glucose | ND |
| (Barley) β-glucan | β-1,3: β-1,4 | Glucose | ND |
| Xylan | β-1,4 | Xylose | ND |
| Carboxymethyl cellulose (CMC) | β-1,4 | Glucose | ND |

ND: Not detected

TABLE 2

Confirmation of Cationic Effect of Gly30B Protein

| Cation | Relative enzymatic activity (%) |
|---|---|
| Control | 100 ± 0.8 |
| $K^+$ | 93.3 ± 1.1 |
| $Na^+$ | 94.5 ± 1.1 |
| $Mg^{2+}$ | 57.0 ± 2.5 |
| $Ca^{2+}$ | 99.0 ± 0.7 |
| $Mn^{2+}$ | 85.0 ± 1.2 |
| $Ni^{2+}$ | 54.7 ± 1.7 |
| $Cu^{2+}$ | 29.4 ± 0.2 |
| $Fe^{2+}$ | 61.5 ± 1.9 |
| $Co^{2+}$ | 70.9 ± 3.1 |

Non-cationic reactive enzymatic activity was taken as 100%
Experimental data was expressed as mean ± standard deviation for three repeated experiments.

<Example 4> Confirmation of Optimum Activity Temperature and pH of Gly30B Protein To find out the optimum temperature and pH for the activity of the Gly30B protein, a mixture of 10.5 µM of the Gly30B protein and 2% (W/V) of laminarin was allowed to react in various temperature ranges (20° C. to 70° C.) and pH conditions (2.0 to 10.0).

Figure 2:
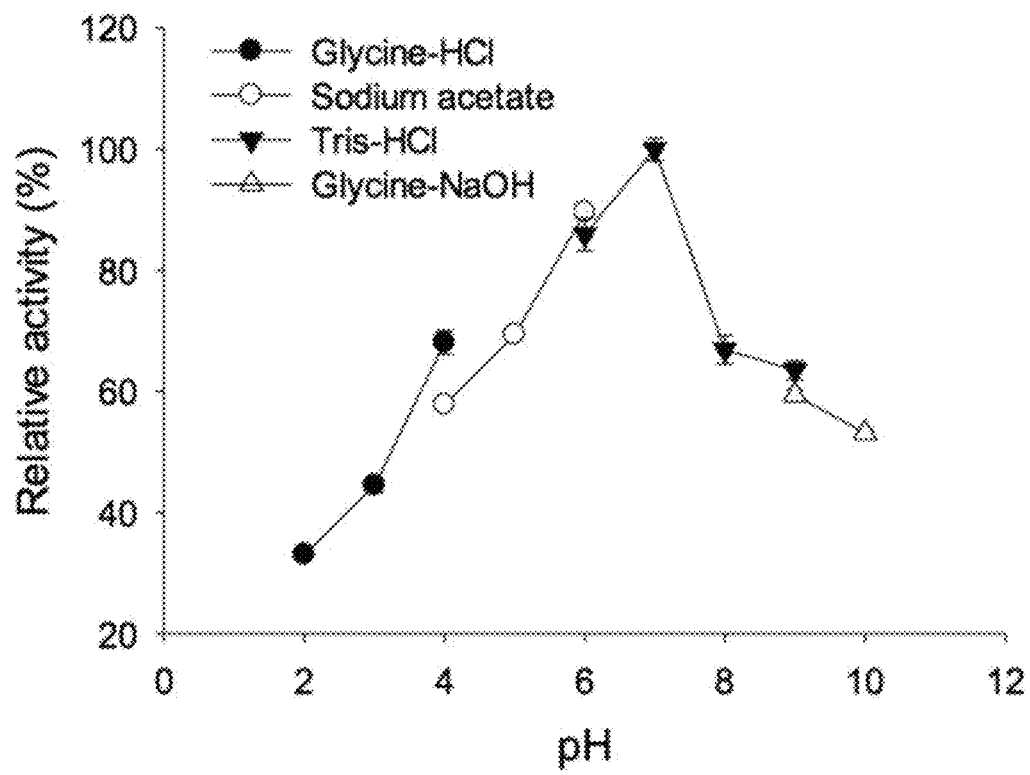
FIG. 2 illustrates results of confirming the optimum active pH of the β-1,6-endoglucanase of the present invention.

FIG. 2 illustrates the relative activity of Gly30B at a pH ranging from 2.0 to 10.0. It was found that the Gly30B protein exhibited the maximum activity at pH 7.0 and that the enzymatic activity rapidly decreased at pHs of less than or greater than pH 7.0. The Gly30B protein exhibited a relative activity of about 40% at pH 2.0 (20 mM glycine-HCl buffer) and a relative activity of about 50% at pH 10.0 (20 mM glycine-NaOH buffer).

Figure 3:
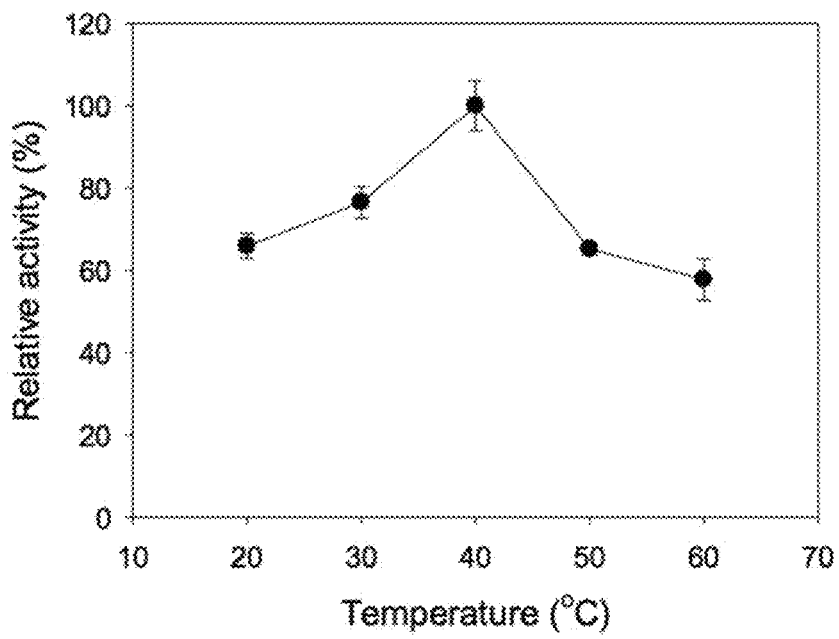
FIG. 3 illustrates results of confirming the optimum active temperature of the β-1,6-endoglucanase of the present invention.
Figure 4:
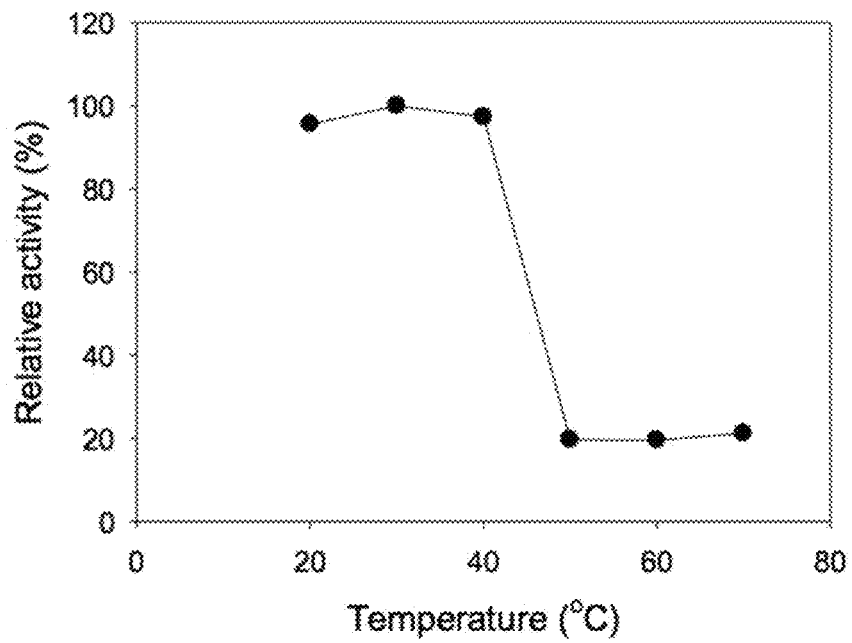
FIG. 4 illustrates results of confirming the thermal stability of the β-1,6-endoglucanase of the present invention.

FIG. 3 illustrates the relative activity of the Gly30B protein at a temperature ranging from 20° C. to 70° C. The enzymatic activity of the Gly30B protein gradually increased with an increase in temperature in the temperature range of 20° C. to 40° C., reaching its maximum at 40° C. The enzymatic activity of the Gly30B protein at reaction temperatures of 20° C. and 60° C. was lower than that observed at 40° C. As a result of examining the thermal stability of the Gly30B protein, it was confirmed that the Gly30B protein was stable at a reaction temperature of 40° C. or less and experienced a remarkable reduction in relative activity at higher temperatures (see FIG. 4). Thus, 40° C.

was determined as the optimum reaction temperature of the Gly30B protein and used in all subsequent experiments.

<Example 5> Confirmation of Enzymatic Reaction Rate of Gly30B Protein

To confirm the enzymatic reaction rate of the Gly30B protein with respect to pustulan and laminarin, the Gly30B protein was allowed to react with 20 mM Tris-HCl buffer containing each substrate at various concentrations, ranging from 0.45% to 9.1%, at pH 7.0 and 40° C.

Figure 5:
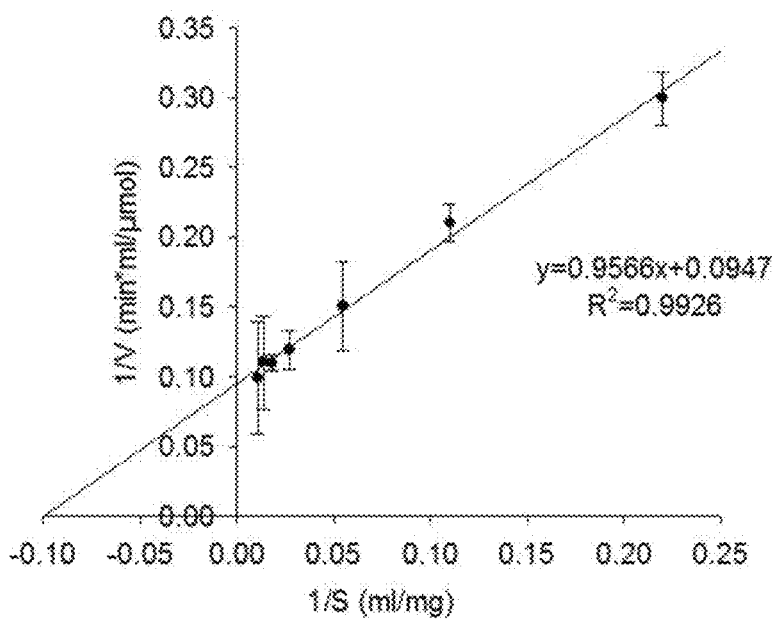
FIG. 5 is a Lineweaver-Burk plot of the β-1,6-endoglucanase of the present invention with respect to the hydrolysis of pustulan.

As a result, it was confirmed from Lineweaver-Burk plot (see FIG. 5) that in the case of the pustulan substrate, Km, Vmax, and Kcat values were 100.8 g/L, 32.8 U/mg, and 28.9 $s^{-1}$, respectively, and in the case of the laminarin substrate, Km, Vmax, and Kcat values were 24.2 g/L, 153.8 U/mg, and 135.6 $s^{-1}$, respectively.

<Example 6> Characterization of Enzymatic Reaction of Gly30B Protein by TLC and HPLC To analyze the enzymatic reaction characteristics of the Gly30B protein according to reaction time, thin layer chromatography (TLC) and high performance liquid chromatography (HPLC) were used.

Reaction products for TLC analysis were developed on a silica gel 60 plate (Merck) using a mixed solvent system consisting of n-butanol, acetic acid, and water (3:2:2, v/v/v), treated with 10% (v/v) of sulfuric acid for visualization, and then heat-treated at 130° C. for 5 minutes.

HPLC analysis was performed using Agilent 1100 HPLC (Agilent) equipped with gel permeation and ligand exchange columns (KS-802; Shodex), and a refractive index detector (Agilent) was used for detection. Sterile water was used as a solvent for the HPLC analysis, the flow rate was set to 0.5 mL/min, and the column temperature was set to 80° C. As standard materials for analysis, laminaribiose (degree of polymerization: DP2), laminaritriose (DP3), laminaritetraose (DP4), laminaripentose (DP5), and laminarihexose (DP6) were used.

Figure 6:
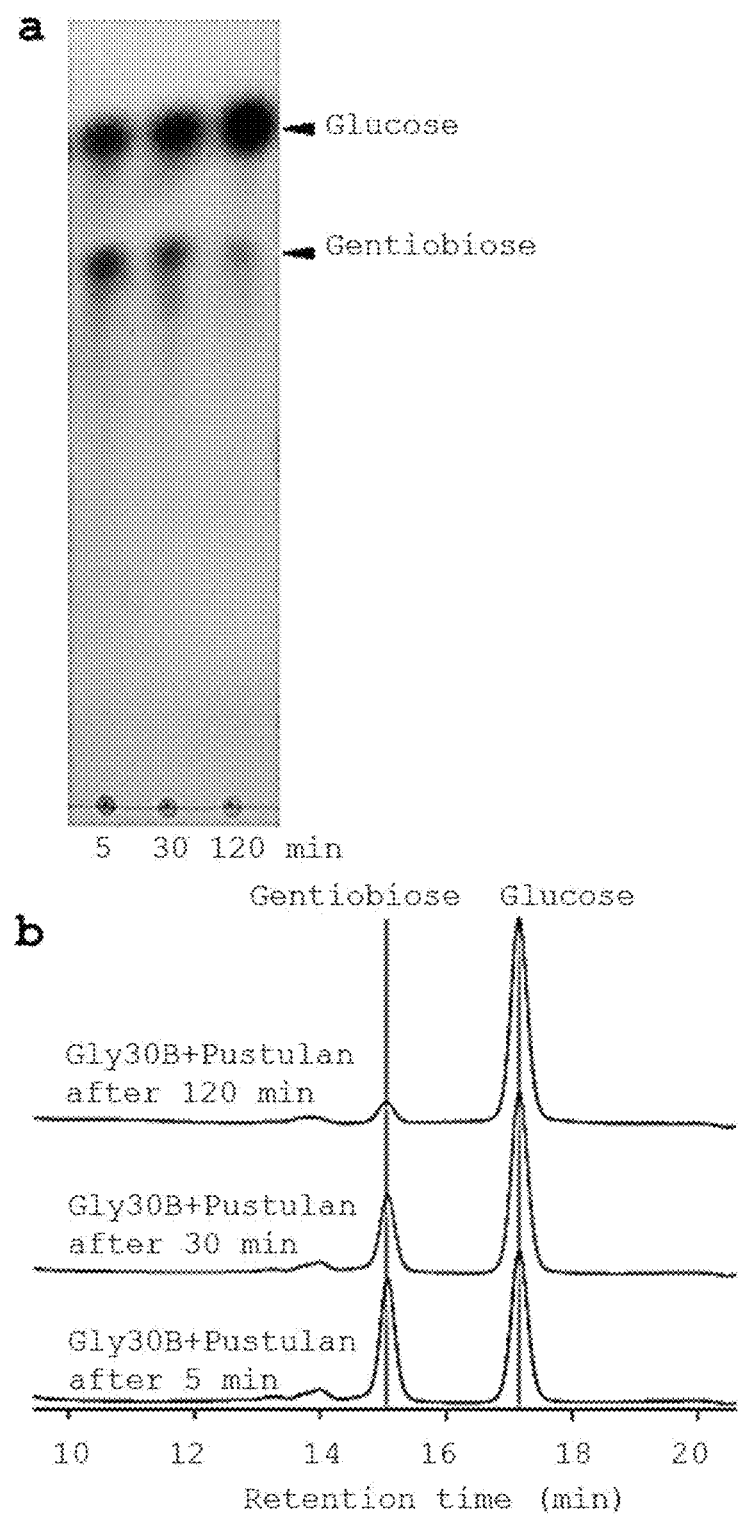
FIG. 6 illustrates TLC (a) and HPLC (b) analysis results of hydrolysis products of the β-1,6-endoglucanase of the present invention with respect to pustulan.

As a result of TLC analysis (see (a) of FIG. 6) of products of the reaction between the Gly30B protein and pustulan, it was confirmed that the production of gentiobiose and glucose began at 5 minutes of the reaction and that gentiobiose was converted into glucose over time. As a result of conducting the reaction for 120 minutes, glucose was confirmed as a main reaction product and a small amount of gentiobiose was confirmed to be produced. As a result of analysis of the same reaction products by HPLC (see (b) of FIG. 6), it was confirmed that, as reaction time elapsed, a peak corresponding to gentiobiose was reduced and a peak corresponding to glucose was produced.

Figure 7:
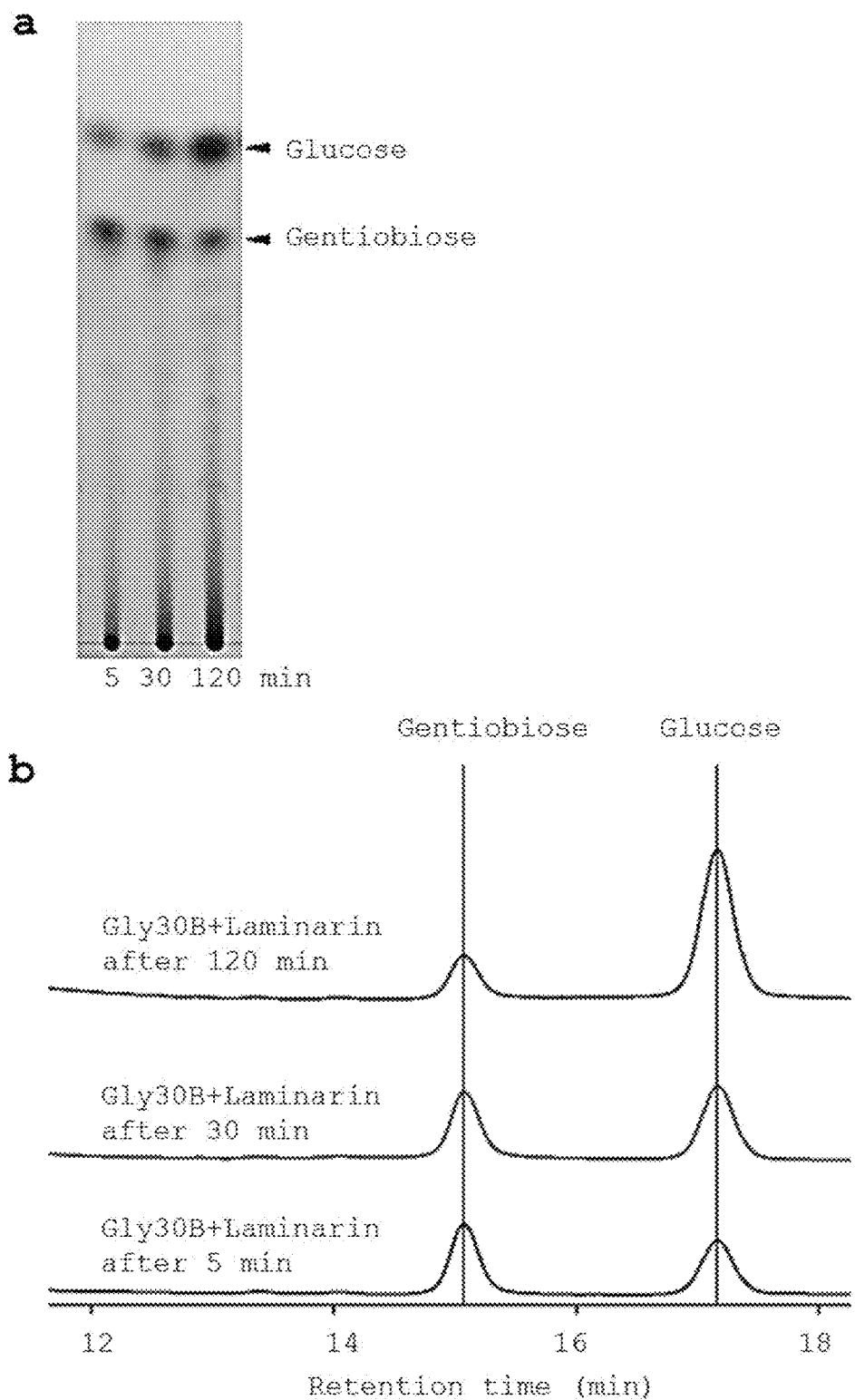
FIG. 7 illustrates TLC (a) and HPLC (b) analysis results of hydrolysis products of the β-1,6-endoglucanase of the present invention with respect to laminarin.

In the case of a reaction between the Gly30B protein and laminarin, it was confirmed that, unlike in the case in which the pustulan substrate was used, the initial laminarin and an oligosaccharide derived therefrom were not completely degraded and remained even after the reaction (see (a) of FIG. 7), and that glucose and gentiobiose were produced (see (b) of FIG. 7). From these results, it was confirmed that the Gly30B protein selectively cleaved β-1,6-linkages and not β-1,3-linkages.

<Example 7> Phylogenetic Analysis of Gly30B Protein

To confirm the novelty of the Gly30B protein, the genetic information of previously known microorganism-derived β-1,6-endoglucanases was obtained from the CAZy database (http://www.cazy.org) and a phylogenetic tree thereof was drawn.

Figure 8:
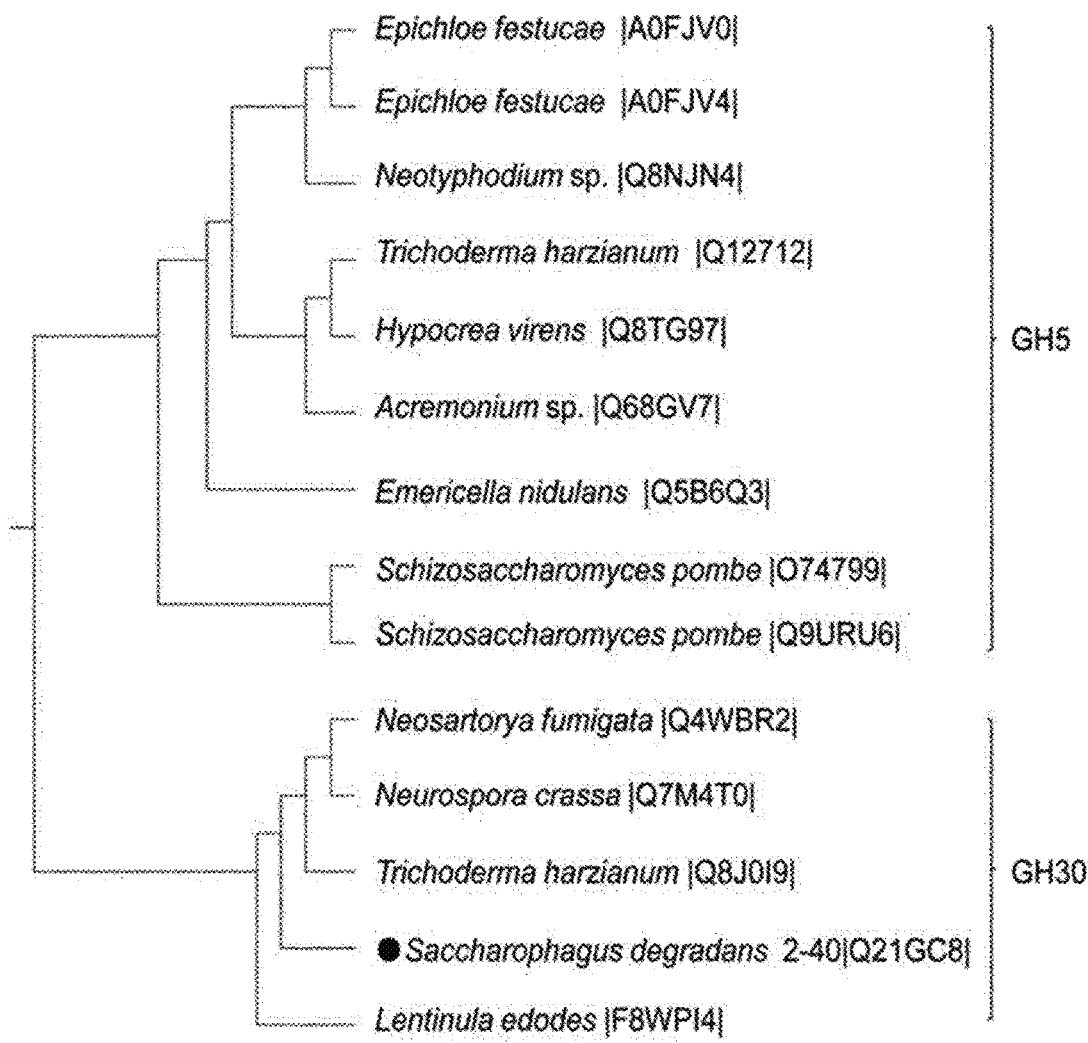
FIG. 8 is a phylogenetic tree of the β-1,6-endoglucanase of the present invention.

As a result, it was confirmed that the Gly30B protein was phylogenetically separated from other previously known β-1,6-endoglucanases, and that the Gly30B protein was the first bacteria-derived enzyme that has never been previously reported (see FIG. 8).

The present invention may be applied to the glucose production field.

What is claimed is:

1. A method of producing gentiobiose or glucose, the method comprising reacting a β-1,6-endoglucanase comprising the amino acid sequence of SEQ ID NO:1 with, as a substrate, one or more selected from the group consisting of laminarin and pustulan to produce gentiobiose and/or glucose as a reaction product,
　　wherein the reaction product does not include an oligosaccharide with other degree of polymerization except for gentiobiose and glucose,
　　wherein the reacting of the β-1,6-endoglucanase and the substrate is performed at a temperature ranging from 20° C. to 45° C. and a pH of 5 to 10, and for 5 minutes to 1 day.

2. The method of claim 1, wherein the β-1,6-endoglucanase is isolated from *Saccharophagus degradans* $2\text{-}40^T$.

3. The method of claim 1, wherein the β-1,6-endoglucanase is obtained from a host cell transformed with a recombinant vector comprising a nucleic acid encoding the β-1,6-endoglucanase, or a cultured product of the host cell.

4. The method of claim 3, wherein the nucleic acid encoding the β-1,6-endoglucanase comprises the base sequence of SEQ ID NO: 2.

* * * * *